United States Patent
Jeon et al.

(10) Patent No.: US 12,187,993 B2
(45) Date of Patent: Jan. 7, 2025

(54) SUSPENSION MAINTENANCE METHOD, SUSPENSION MAINTENANCE APPARATUS, AND BIO 3D PRINTER INCLUDING SAME

(71) Applicant: CLECELL CO., LTD., Gyeonggi-do (KR)

(72) Inventors: Kyoung Whee Jeon, Seoul (KR); Min Hyuck Kang, Seoul (KR); Hyo Kyoung Bae, Gyeonggi-do (KR)

(73) Assignee: CLECELL CO., LTD., Gyeonggi-do (KR)

( * ) Notice: Subject to any disclaimer, the term of this patent is extended or adjusted under 35 U.S.C. 154(b) by 673 days.

(21) Appl. No.: 17/419,267

(22) PCT Filed: Jan. 10, 2020

(86) PCT No.: PCT/KR2020/000528
§ 371 (c)(1),
(2) Date: Jun. 28, 2021

(87) PCT Pub. No.: WO2020/184829
PCT Pub. Date: Sep. 17, 2020

(65) Prior Publication Data
US 2022/0073849 A1    Mar. 10, 2022

(30) Foreign Application Priority Data

Mar. 14, 2019 (KR) .................. 10-2019-0029371
Aug. 1, 2019 (JP) ...................... 2019-142280

(51) Int. Cl.
*C12M 3/00* (2006.01)
*B29C 64/209* (2017.01)
(Continued)

(52) U.S. Cl.
CPC ........... *C12M 21/08* (2013.01); *B29C 64/209* (2017.08); *B29C 64/314* (2017.08); *B33Y 30/00* (2014.12); *B33Y 40/10* (2020.01); *C12M 33/04* (2013.01)

(58) Field of Classification Search
CPC ...... C12M 33/04; C12M 27/24; C12M 29/08; C12M 21/08; B01L 3/02–0206;
(Continued)

(56) References Cited

U.S. PATENT DOCUMENTS 6,059,441 A * 5/2000 Colin .................... B01F 33/405
366/101
7,850,365 B1 * 12/2010 Much ..................... C12M 27/20
435/296.1
(Continued)

FOREIGN PATENT DOCUMENTS

JP    2006288244 A  * 10/2006  ............ C12M 23/08
JP    6594582        10/2019
(Continued)

OTHER PUBLICATIONS

"International Search Report (Form PCT/ISA/210) of PCT/KR2020/000528," mailed on May 4, 2020, with English translation thereof, pp. 1-6.

*Primary Examiner* — Seyed Masoud Malekzadeh
*Assistant Examiner* — Jennifer L Groux
(74) *Attorney, Agent, or Firm* — JCIPRNET (57) ABSTRACT

An apparatus for maintaining a cell suspension of a biomaterial for a bio 3D printer includes: a body detachably coupled to a syringe; a vent formed inside the body in a longitudinal direction of the syringe; a pipette fixture extending downward from the body and formed in a tapered shape whose outer diameter decreases downwardly; an air discharge port formed inside the pipette fixture, connected to the vent, and communicated into the syringe; a syringe
(Continued)

fixing arm protruding from the body in a direction perpendicular to the longitudinal direction of the syringe to surround an upper flange of the syringe and fixed to the syringe; and a pipette coupled to the pipette fixture and having a hollow tapered shape whose inner diameter decreases downwardly and having a lower end positioned in an outlet of the syringe.

16 Claims, 7 Drawing Sheets

(51) Int. Cl.
*B29C 64/314* (2017.01)
*B33Y 30/00* (2015.01)
*B33Y 40/10* (2020.01)
*C12M 1/26* (2006.01)

(58) Field of Classification Search
CPC ............ B01L 2300/048; B29C 64/205; B29C 64/209; B29C 64/106; B29C 64/112; G01N 35/1009; G01N 35/10; G01N 2035/1058; G01N 2035/106; B33Y 40/10; B33Y 30/00; B01F 25/435; B01F 25/305; B01F 25/31; B01F 33/4051; B01F 33/40511; B01F 23/2323; B01F 23/23231; B01F 23/232311; B01F 25/42; B01F 25/43; B01F 33/40; B01F 33/403; B01F 33/405

See application file for complete search history.

(56) References Cited

U.S. PATENT DOCUMENTS

| | | | |
|---|---|---|---|
| 2007/0035105 A1 | 2/2007 | Yale | |
| 2013/0017129 A1* | 1/2013 | Shioyama | B01L 3/502 422/513 |
| 2020/0015509 A1* | 1/2020 | Weinstein | B33Y 30/00 |
| 2020/0139704 A1* | 5/2020 | Muramatsu | B05B 17/0676 |
| 2020/0377845 A1* | 12/2020 | Watanabe | B01F 31/26 |
| 2022/0118681 A1* | 4/2022 | Sexton | B29C 64/307 |

FOREIGN PATENT DOCUMENTS

| | | | |
|---|---|---|---|
| KR | 20020060620 | 7/2002 | |
| KR | 20170005450 | 1/2017 | |
| KR | 101828345 | 3/2018 | |
| KR | 20180032597 | 3/2018 | |
| KR | 20180067497 | 6/2018 | |
| KR | 20190029371 | 3/2019 | |
| WO | WO-2014110250 A1 * | 7/2014 | ........ B29C 47/0004 |
| WO | 2015175457 | 11/2015 | |
| WO | 2017011854 | 1/2017 | |

\* cited by examiner

SUSPENSION MAINTENANCE METHOD, SUSPENSION MAINTENANCE APPARATUS, AND BIO 3D PRINTER INCLUDING SAME

CROSS-REFERENCE TO RELATED APPLICATION

This application is a 371 application of the International PCT application serial no. PCT/KR2020/000528, filed on Jan. 10, 2020, which claims the priority benefits of Korea Patent Application No. 10-2019-0029371, filed on Mar. 14, 2019, and Japan Patent Application No. 2019-142280, filed on Aug. 1, 2019. The entirety of each of the above-mentioned patent applications is hereby incorporated by reference herein and made a part of this specification.

TECHNICAL FIELD

The present invention relates to a suspension maintenance method, a suspension maintenance apparatus, and a bio 3D printer including the same.

BACKGROUND ART

A 3D printer includes a frame constituting an XYZ axis and a nozzle that sprays liquid or powdery materials capable of stacking a three-dimensional shape to a planar shape, According to methods, 3D printers include, for example, a Cartesian method, a Mendelian method, a delta method, and a core XY method.

In the Cartesian method, a bed moves along X and Y axes and a nozzle moves along a Z axis to implement 3D printing. In the Mendelian method, the bed moves along the Z axis and the nozzle moves along the X and Y axes to implement 3D printing. In the delta method, the nozzle moves along the X, Y, and Z axes to implement 3D printing. In the core XY method, the nozzle moves along the X and Y axis directions by a belt connected by two motors, and the bed moves along the Z direction. Recently, the core XY method capable of controlling a position of the nozzle most precisely has been widely used.

A bio 3D printer is a device structurally modified to discharge a biomaterial through the nozzle of the 3D printer and generate a living tissue or organ in three dimensions.

Such a bio 3D printer includes the nozzle in the form of a dispenser for discharging the biomaterial. The bio 3D printer fills the nozzle with a biomaterial in the form of a viscous fluid such as collagen and gelatin. The bio 3D printer uses a method of connecting a pneumatic system to the nozzle filled with the biomaterial in the form of fluid to push and discharge the biomaterial.

An example of the bio 3D printer is disclosed in Patent Document 1.

In order for the bio 3D printer to print a biomaterial such as cells, a suspension in which a culture medium and cells are uniformly mixed is prepared. The prepared biomaterial suspension is accommodated in a syringe, and the biomaterial supplied from the syringe is output on a substrate in a desired shape by a spray nozzle.

The biomaterial contained in the syringe must maintain a uniform mixture of the cells and the culture medium, but as time passes, the cells sink to the bottom of the culture medium due to gravity. As such, the sunken cells aggregate and adhere to the bottom or the wall of the syringe, so that the cells cannot escape from the syringe or are discharged as a lump, thereby clogging the nozzle.

In order to prevent such a problem from occurring, the syringe must be continuously shaken or the biomaterial contained in the syringe must be repeatedly pipetted. Conventional bio 3D printers have not solved this problem. Accordingly, the conventional bio 3D printer has a limitation of using only a low viscous culture medium to make it difficult for the biomaterial to sink to the bottom of the syringe.

PRIOR ART DOCUMENTS

[Patent Document] 1: KR Registration Patent No. 1828345

DESCRIPTION OF EMBODIMENTS

Technical Problem

The present invention provides a cell suspension maintenance method capable of periodically pipetting a biomaterial coupled to a syringe so that the biomaterial contained in the syringe may continuously maintain a suspension state.

The present invention also provides a cell suspension maintenance apparatus capable of periodically pipetting a biomaterial coupled to a syringe so that the biomaterial contained in the syringe may continuously maintain a suspension state.

The present invention also provides a cell suspension maintenance system capable of periodically pipetting a biomaterial coupled to a syringe so that the biomaterial contained in the syringe may continuously maintain a suspension state.

The present invention also provides a bio 3D printer having a cell suspension maintenance function capable of periodically pipetting a biomaterial coupled to a syringe so that the biomaterial contained in the syringe may continuously maintain a suspension state.

The problem of the present invention is not limited to those mentioned above, and other problems that are not mentioned will be clearly understood by those of ordinary skill in the art from the following description.

Solution to Problem

According to an aspect of the present invention, there is provided a suspension maintenance apparatus including: a body detachably coupled to a syringe; a vent formed inside the body in a longitudinal direction of the syringe; a pipette fixture extending downward from the body and formed in a tapered shape whose outer diameter decreases downwardly; an air discharge port formed inside the pipette fixture, connected to the vent, and communicated into the syringe; a syringe fixing arm protruding from the body in a direction perpendicular to the longitudinal direction of the syringe to surround an upper flange of the syringe and fixed to the syringe; and a pipette coupled to the pipette fixture and having a hollow tapered shape whose inner diameter decreases downwardly and having a lower end positioned in an outlet of the syringe.

The suspension maintenance apparatus includes a sealing ring coupling groove formed concavely in a side surface of the body and extending in a circumferential direction of the syringe; and an annular sealing ring coupled to the sealing ring coupling groove, wherein an outer circumferential surface of the sealing ring is tightly coupled to an inner circumferential surface of the syringe in an elastically pressed state.

The air discharge port extends in a direction perpendicular to the longitudinal direction of the syringe, and is configured to eject air discharged through the air discharge port toward an inner wall of the syringe.

The syringe fixing arm includes a support arm protruding from the body symmetrically from each other in a direction perpendicular to the longitudinal direction of the syringe and contacting an upper surface of the upper flange of the syringe and an arm cover contacting a lower surface of the upper flange of the syringe and detachably coupled to the support arm.

The arm cover includes a separation prevention stopper that prevents the syringe fixing arm from being separated from the syringe by being caught by the upper flange of the syringe.

The pipette has an upper end coupled to the pipette fixture and sealed by the pipette fixture so that air is injected into the pipette through an upper portion of the pipette.

The suspension maintenance apparatus further includes a hose coupling member configured to couple a hose for supplying a pneumatic pressure to an upper portion of the vent.

According to another aspect of the present invention, there is provided a syringe including the suspension maintenance apparatus.

According to another aspect of the present invention, there is provided a bio 3D printer including a syringe including the suspension maintenance apparatus and having an outlet connected to a nozzle injecting a biomaterial; and a pneumatic pressure supply apparatus for supplying a preset pneumatic pressure to the suspension maintenance apparatus.

The pneumatic pressure supply apparatus includes an air compressor for supplying air at a high pressure, and an electropneumatic regulator having one side connected to the suspension maintenance apparatus and the other side connected to the air compressor to convert the air supplied at the high pressure from the air compressor to a preset pneumatic pressure and supplying the pneumatic pressure to the suspension maintenance apparatus.

The pneumatic pressure supply apparatus includes a precision pump.

The bio 3D printer further includes an air dryer installed between the electropneumatic regulator and the air compressor to remove water vapor contained in the air supplied at the high pressure from the air compressor.

The bio 3D printer further includes a controller controlling the electropneumatic regulator to periodically apply pneumatic pressure to the suspension maintenance apparatus at a preset minimum pressure and a preset maximum pressure during a time when the biomaterial accommodated in the syringe is not discharged downward from the syringe.

The bio 3D printer further includes a controller controlling the precision pump to periodically apply pneumatic pressure to the suspension maintenance apparatus at a preset minimum pressure and a preset maximum pressure during a time when the biomaterial accommodated in the syringe is not discharged downward from the syringe.

The minimum pressure is equal or higher than an atmospheric pressure, and the maximum pressure is a pressure higher than the atmospheric pressure by a predetermined pressure and higher than the minimum pressure.

According to another aspect of the present invention, there is provided a suspension state maintenance method of a biomaterial accommodated in a syringe by controlling an electropneumatic regulator in a suspension maintenance apparatus including: a body detachably coupled to the syringe; a vent formed inside the body in a longitudinal direction of the syringe; a pipette fixture extending downward of the body and formed in a tapered shape whose outer diameter decreases downwardly; an air discharge port formed inside the pipette fixture, connected to the vent, and communicated into the syringe; a syringe fixing arm protruding from the body in a direction perpendicular to the longitudinal direction of the syringe to surround an upper flange of the syringe and fixed to the syringe; and a pipette coupled to the pipette fixture and having a hollow tapered shape whose inner diameter decreases downwardly and having a lower end positioned in an outlet of the syringe, and a bio 3D printer including a syringe including the suspension maintenance apparatus and having an outlet connected to a nozzle injecting the biomaterial, an air compressor for supplying air at a high pressure, and the electropneumatic regulator having one side connected to the suspension maintenance apparatus and the other side connected to the air compressor to convert the air supplied at the high pressure from the air compressor to a preset pneumatic pressure and supplying the pneumatic pressure to the suspension maintenance apparatus, the suspension state maintenance method including: applying a predetermined minimum pressure to the suspension maintenance apparatus coupled to the syringe containing the biomaterial; gradually increasing the pneumatic pressure in the suspension maintenance apparatus to a maximum pressure greater than the minimum pressure; gradually reducing the pneumatic pressure from the maximum pressure to the minimum pressure; and repeating increasing the pneumatic pressure and reducing the pneumatic pressure for a predetermined period.

The minimum pressure is equal or higher than an atmospheric pressure, and the maximum pressure is a pressure higher than the atmospheric pressure by a predetermined pressure and higher than the minimum pressure.

In the present specification, each embodiment is described independently, but each embodiment can be combined with each other, and a combined embodiment is also included in the scope of the present invention.

The above summary is for illustrative purposes only and is not intended to be limiting in any way. In addition to the above-described illustrative aspects, embodiments, and features, additional aspects, embodiments, and features will be apparent by reference to the drawings and the detailed description below.

Advantageous Effects of Disclosure

The at least one embodiment of the present invention has an effect of providing a cell suspension maintenance method capable of periodically pipetting a biomaterial adhered to a syringe so that the biomaterial contained in the syringe may continuously maintain a suspension state.

The at least one embodiment of the present invention has an effect of providing a cell suspension maintenance apparatus capable of periodically pipetting a biomaterial adhered to a syringe so that the biomaterial contained in the syringe may continuously maintain a suspension state.

The at least one embodiment of the present invention has an effect of providing a cell suspension maintenance system capable of periodically pipetting a biomaterial adhered to a syringe so that the biomaterial contained in the syringe may continuously maintain a suspension state.

The at least one embodiment of the present invention has an effect of providing a bio 3D printer having a cell suspension maintenance function capable of periodically pipetting a biomaterial adhered to a syringe so that the biomaterial contained in the syringe may continuously maintain a suspension state.

The effects of the present invention are not limited to those mentioned above, and other effects not mentioned will be clearly understood by those of ordinary skill in the art from the following description.

BEST MODE

Hereinafter, embodiments of the present invention will be described in detail with reference to the accompanying drawings.

Figure 1:
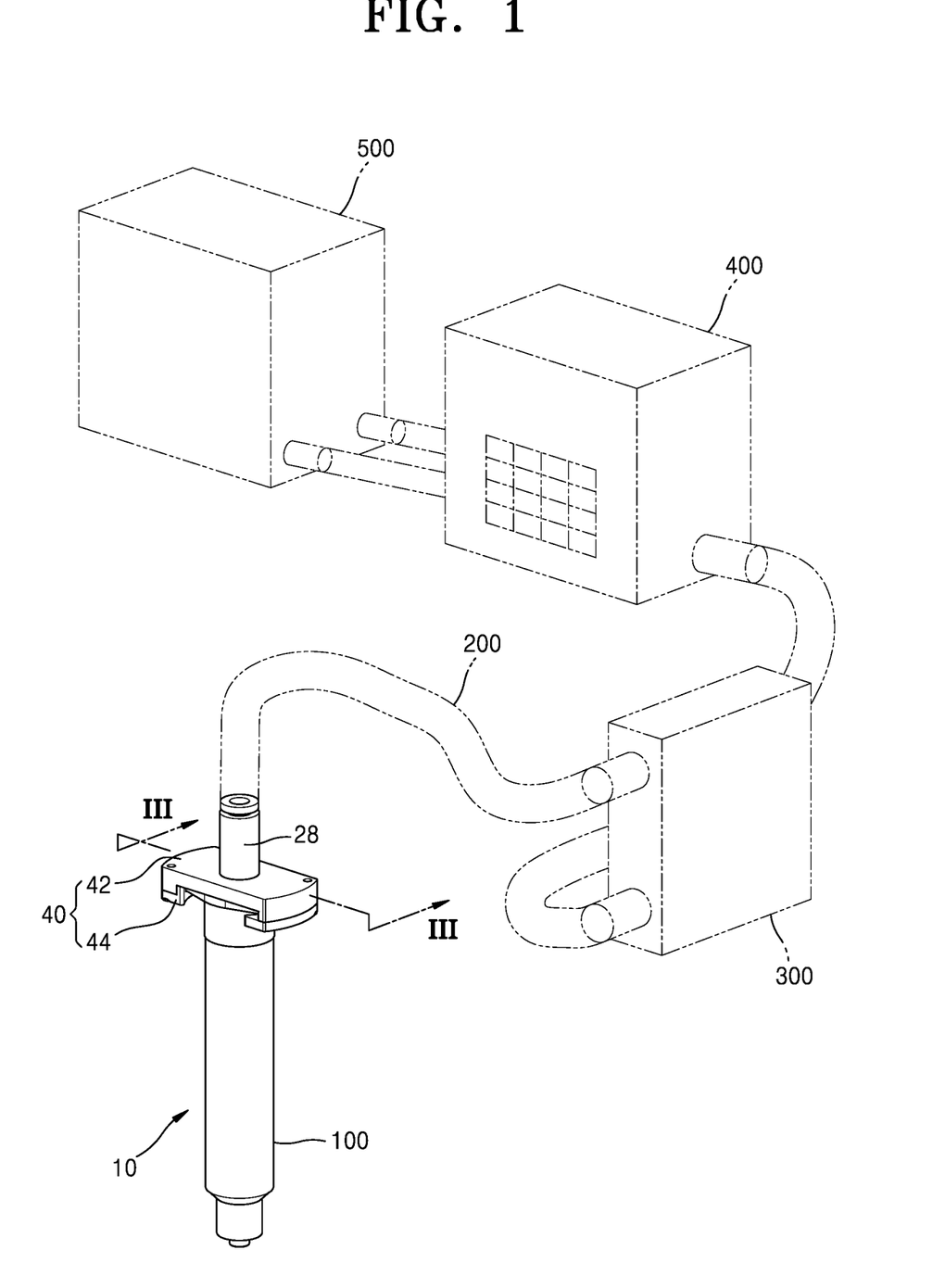
FIG. 1 is a perspective view of an apparatus for maintaining a cell suspension of a biomaterial for a bio 3D printer according to at least one embodiment of the present invention.
Figure 2:
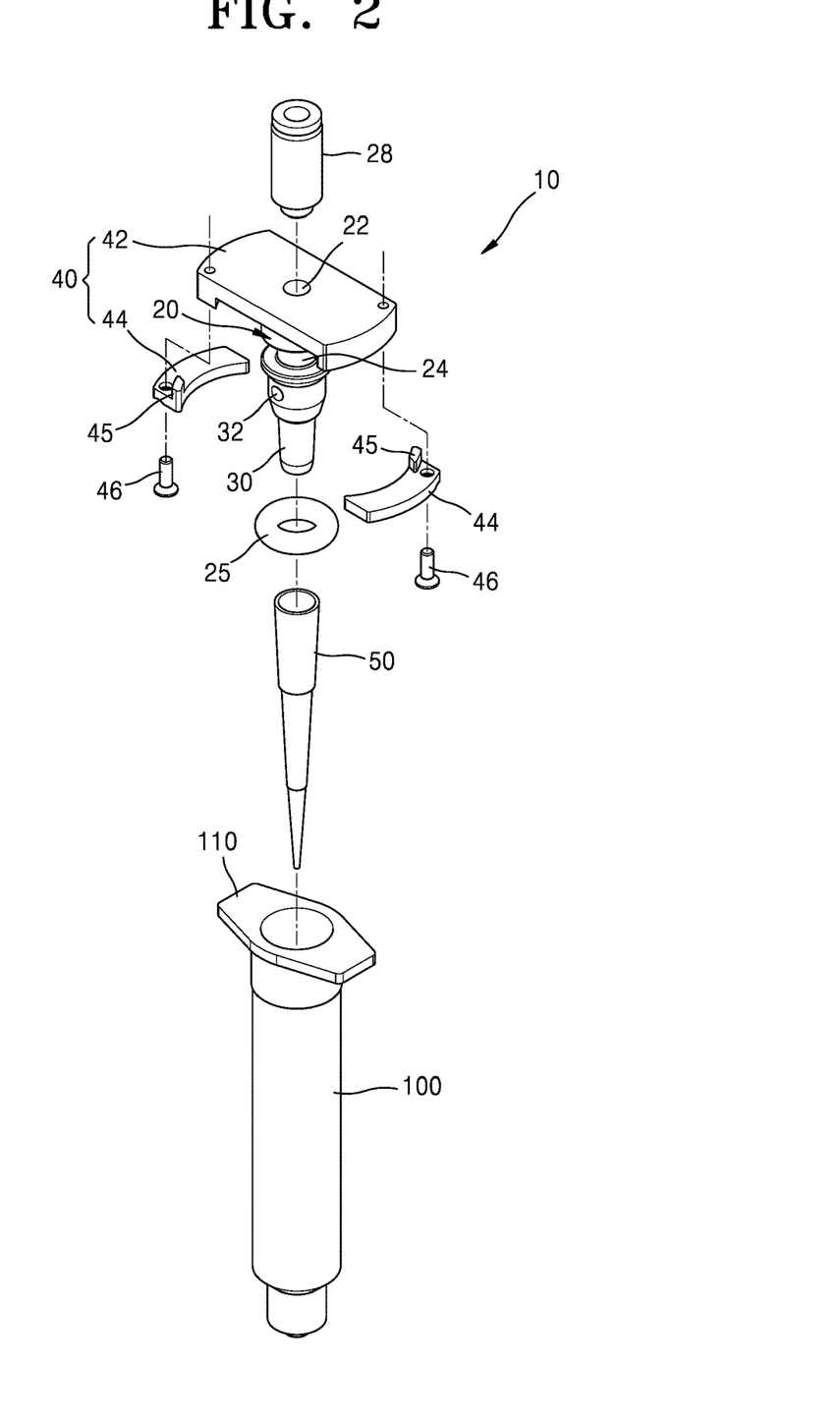
FIG. 2 is an exploded perspective view of the device shown in FIG. 1.
Figure 3:
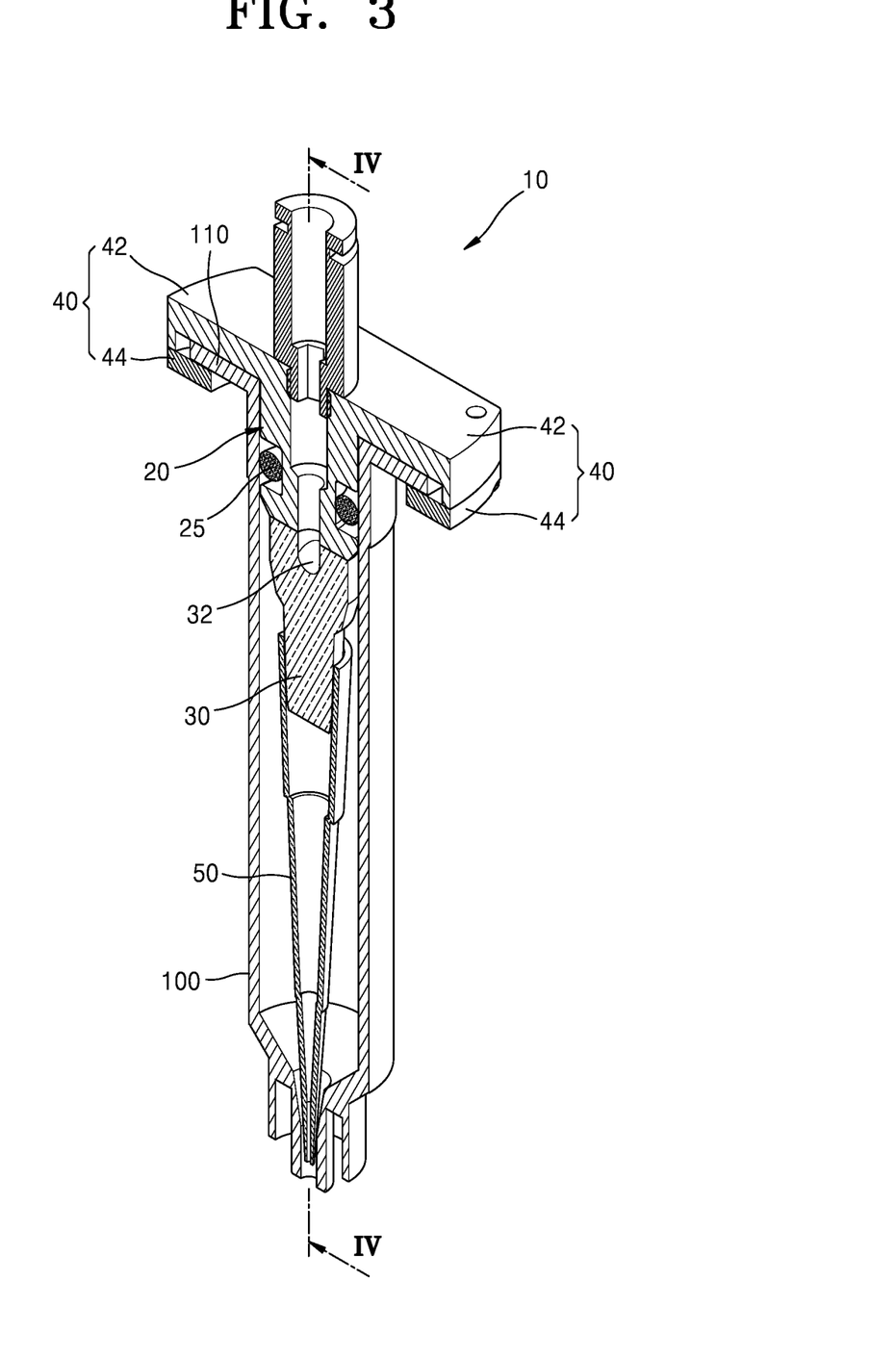
FIG. 3 is a cross-sectional view taken along a line III-III shown in FIG. 1.
Figure 4:
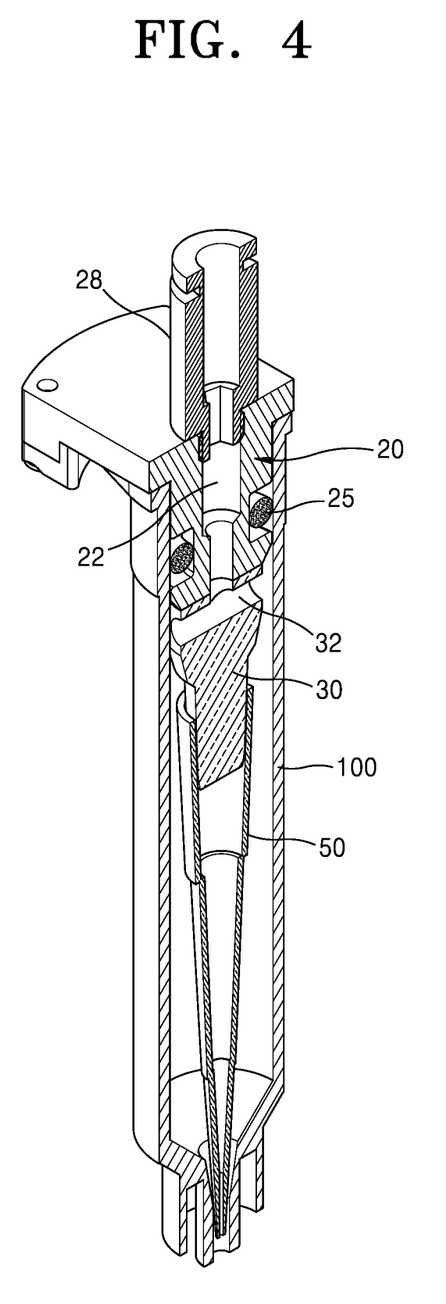
FIG. 4 is a cross-sectional view taken along a line IV-IV shown in FIG. 3.

FIG. 1 is a perspective view of an apparatus for maintaining a cell suspension of a biomaterial for a bio 3D printer according to at least one embodiment of the present invention. FIG. 2 is an exploded perspective view of the device shown in FIG. 1. FIG. 3 is a cross-sectional view taken along line III-III shown in FIG. 1. FIG. 4 is a cross-sectional view taken along line IV-IV shown in FIG. 3.

Referring to FIGS. 1 to 4, the apparatus 10 for maintaining the cell suspension of the biomaterial for the bio 3D printer according to at least one embodiment of the present invention includes a body 20, a pipette fixture 30, and a syringe fixing arm 40, a pipette 50, and a vent 22.

The body 20 may be used in a form coupled to a syringe 100 as shown in FIGS. 3 to 6. The syringe 100 is a syringe-shaped member. The syringe 100 is provided so that an upper flange 110 is formed symmetrically in a direction perpendicular to a longitudinal direction of the syringe 100 in an upper end of the syringe 100. The body 20 is detachably coupled to the syringe 100.

The body 20 may be slidably coupled along an inner circumferential surface of the syringe 100. The vent 22 is provided in the body 20. The vent 22 is formed in the longitudinal direction of the syringe 100 and is configured to allow air to communicate with the outside. The vents 22 passes through upper and lower ends of the body 20.

The body 20 may be made of an aluminum alloy or a hard synthetic resin material. The body 20 may be made of an engineering synthetic resin having excellent heat resistance, chemical resistance, and abrasion resistance, such as polyether ether ketone (PEEK).

A sealing ring coupling groove 24 is provided in the body 20. The sealing ring coupling groove 24 is formed concavely in the side of the body 20. The sealing ring coupling groove 24 is an annular groove extending in a circumferential direction of the syringe 100. An annular sealing ring 25 is coupled to the sealing ring coupling groove 24. An outer circumferential surface of the sealing ring 25 is disposed to protrude outward from an outer circumferential surface of the body 20. The outer circumferential surface of the sealing ring 25 is coupled to the inner circumferential surface of the syringe 100 in an elastically pressed state. The inflow of a biomaterial 120 between the body 20 and the inner surface of the syringe 100 is blocked by the sealing ring 25.

The pipette fixture 30 is formed extending downward of the body 20. It is preferable that the pipette fixture 30 has a tapered shape whose outer diameter decreases downwardly. An air discharge port 32 is provided in the pipette fixture 30.

The air discharge port 32 is connected to the vent 22. A lower end of the air discharge port 32 is formed in a direction perpendicular to the longitudinal direction of the syringe 100. Specifically, lower ends of the air discharge port 32 are provided to extend in opposite directions to each other. Air discharged through the air discharge port 32 is supplied to the inner space of the syringe 100. Air discharged through the air discharge port 32 is ejected toward an inner wall of the syringe 100.

The pipette fixture 30 may be made of the same material as the body 20. The pipette fixture 30 may be sterilized by immersed in a high pressure sterilizer such as an autoclave. The body 20 and the pipette fixture 30 may be manufactured as separate members and then combined into a integrated structure by bonding, welding, or thermal fusion.

The syringe fixing arm 40 is formed extending from the body 20 to the side of the body 20. The syringe fixing arm 40 may be made of the same material as the body 20. The syringe fixing arm 40 is formed protruding from the body 20 in a direction perpendicular to the longitudinal direction of the syringe 100. The syringe fixing arm 40 is fixed to the syringe 100 in a form surrounding the upper flange 110 of the syringe 100. The syringe fixing arm 40 includes a support arm 42 and an arm cover 44.

The support arms 42 are formed to protrude from the body 20 symmetrically from each other in a direction perpendicular to the longitudinal direction of the syringe 100. The support arm 42 is installed to contact an upper surface of the upper flange of the syringe 100. A hole for fixing the arm cover 44 to be described later is formed in the support arm 42.

The arm cover 44 is installed to contact the lower surface of the upper flange 110 of the syringe 100. The arm cover 44 is detachably fixed to the support arm 42. More specifically, the arm cover 44 may be detachably fixed to the support arm 42 through a member such as a screw 46. A separation prevention stopper 45 that prevents the syringe fixing arm 40 from being unexpectedly separated from the syringe 100 by being caught by the upper flange 110 of the syringe 100 is provided in the arm cover 44. The arm covers 44 are each provided on left and right sides of the syringe 100.

The pipette 50 is a hollow tube-shaped member whose inner diameter decreases from the top to the bottom. The pipette 50 is coupled to the pipette fixture 30. An upper end of the pipette 50 is coupled to the pipette fixture 30. A lower end of the pipette 50 is disposed in a lower portion of an outlet of the syringe 100. The upper portion of the pipette 50 is sealed by the pipette fixture 30. Therefore, air cannot be injected into the pipette 50 through the upper portion of the pipette 50.

It is preferable that a structure in which a pneumatic pressure supply hose 200 may be coupled in a one-touch form is provided in the upper portion of the vent 22. In at least one embodiment of the present invention, a one-touch hose coupling member 28 that may be detachably coupled to the body 20 is provided on the upper portion of the vent 22. The one-touch coupling structure of the hose 200 may employ a known conventional structure, and thus a detailed description thereof will be omitted.

In at least one embodiment of the present invention, during a time when the biomaterial 120 accommodated in the syringe 100 is not discharged downward from the syringe 100, pneumatic pressure between preset minimum pressure and maximum pressure is periodically applied to the upper end of the vent 22.

The hose 200 for supplying air is coupled to the upper end of the vent 22. In at least one embodiment of the present invention, the hose 200 is connected to an electropneumatic regulator 300. The electropneumatic regulator 300 is a known device that precisely controls the pressure of air discharged in proportion to an electrical signal, and serves to control the pressure of air supplied to the body 20. The electropneumatic regulator 300 serves to automatically adjust the pressure of air supplied to the body 20 to a preset value by an electronic control device. The electropneumatic regulator 300 may be configured by employing a known commercial product.

Air supplied to the electropneumatic regulator 300 is provided by an air compressor 500. The air compressor 500 compresses air at a high pressure and supplies the air to the electropneumatic regulator 300. The electropneumatic regulator 300 converts the air of high pressure supplied from the air compressor 500 into a set pneumatic pressure and supplies the air to the body 20. The air compressor 500 may be configured by employing a known commercial product.

It is preferable that an air dryer 400 is installed between the electropneumatic regulator 300 and the air compressor 500. The air dryer 400 is a device that purifies air supplied to the electropneumatic regulator 300 by reducing a temperature of water vapor contained in the air of high pressure supplied from the air compressor 500 in the compressed air into through, for example, a cooler, and changing and removing the water vapor in the compressed air to condensate water. The air dryer 400 may be configured by employing a known device.

In the above, an example of controlling the pressure of air supplied to the body 20 using an electropneumatic regulator is described, but the present invention is not limited thereto, and, for example, a precision pump (not shown) may be used to control the pressure of air supplied to the body 20.

A method of installing the apparatus 10 for maintaining the cell suspension of the biomaterial including the above components in the syringe 100 will be described.

First, the pipette 50 is coupled to the pipette fixture 30. Then, a certain amount of the biomaterial 120 is injected into the syringe 100. From the upper side of the syringe 100, the pipette fixture 30 to which the pipette 50 is fixed and the body 20 are inserted into the syringe 100. The lower end of the pipette 50 is located in the lower portion of the outlet of the syringe 100.

The body 20 is elastically supported and fixed to the syringe 100 by the sealing ring 25. The support arm 42 is seated so as to contact an upper surface of the upper flange 110 of the syringe 100. In that state, the arm cover 44 is fixed to the support arm 42 using a screw 46 in a state in which the arm cover 44 is in contact with the lower surface of the upper flange 110 of the syringe 100. Accordingly, the support arm 42 and the arm cover 44 fix the upper flange 110 of the syringe 100 in a sandwich shape.

Accordingly, the body 20 is firmly fixed to the syringe 100 so that the body 20 is not separated from the syringe 100 even if the pressure inside the syringe 100 changes.

A method of maintaining a cell suspension state using the above-described apparatus 10 for maintaining the cell suspension of the biomaterial will be described.

The outlet of the syringe 100 is connected to a nozzle (not shown) that precisely sprays the biomaterial 120. The air of high pressure supplied to the air compressor 500 is supplied to the electropneumatic regulator 300 in a state in which moisture is removed by the air dryer 400.

The electropneumatic regulator 300 supplies air of a constant pressure to the vents 22 of the body 20. The air supplied by the vent 22 pressurizes the biomaterial 120 accommodated in the syringe 100 through the air discharge port 32. Accordingly, when the nozzle (not shown) is opened, the biomaterial 120 passes through the nozzle through the outlet of the syringe 100 and is output to a substrate.

Figure 5:
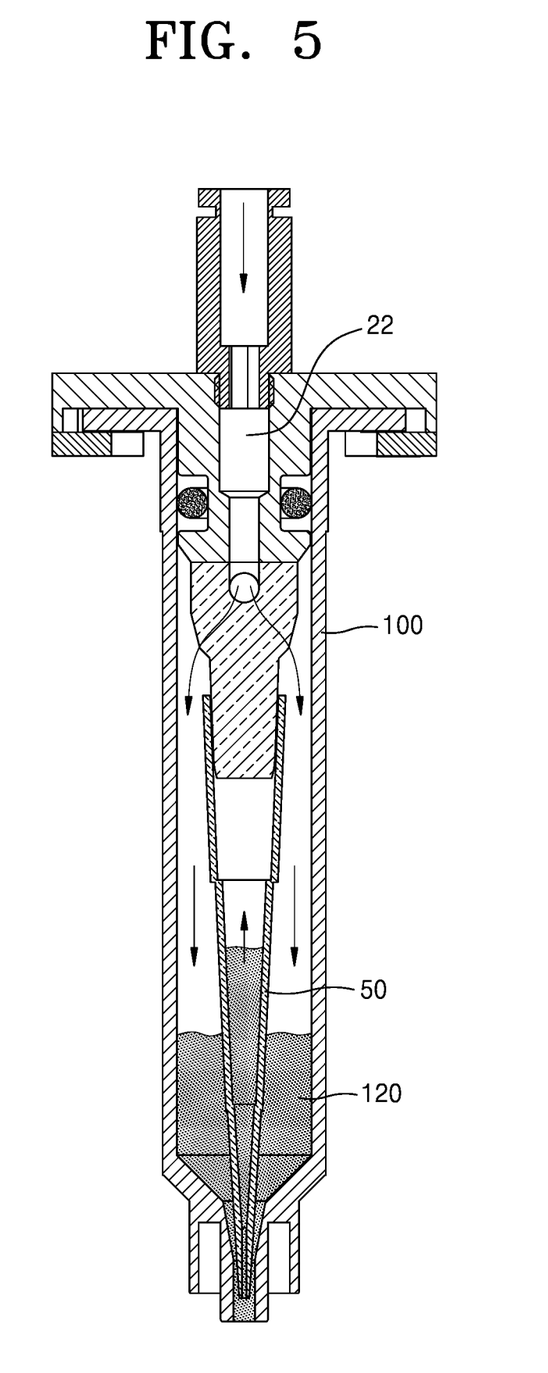
FIG. 5 is a diagram corresponding to FIG. 3 and is a cross-sectional view showing a level of a biomaterial in a state in which a pneumatic pressure supplied to a vent reaches a maximum pressure.
Figure 6:
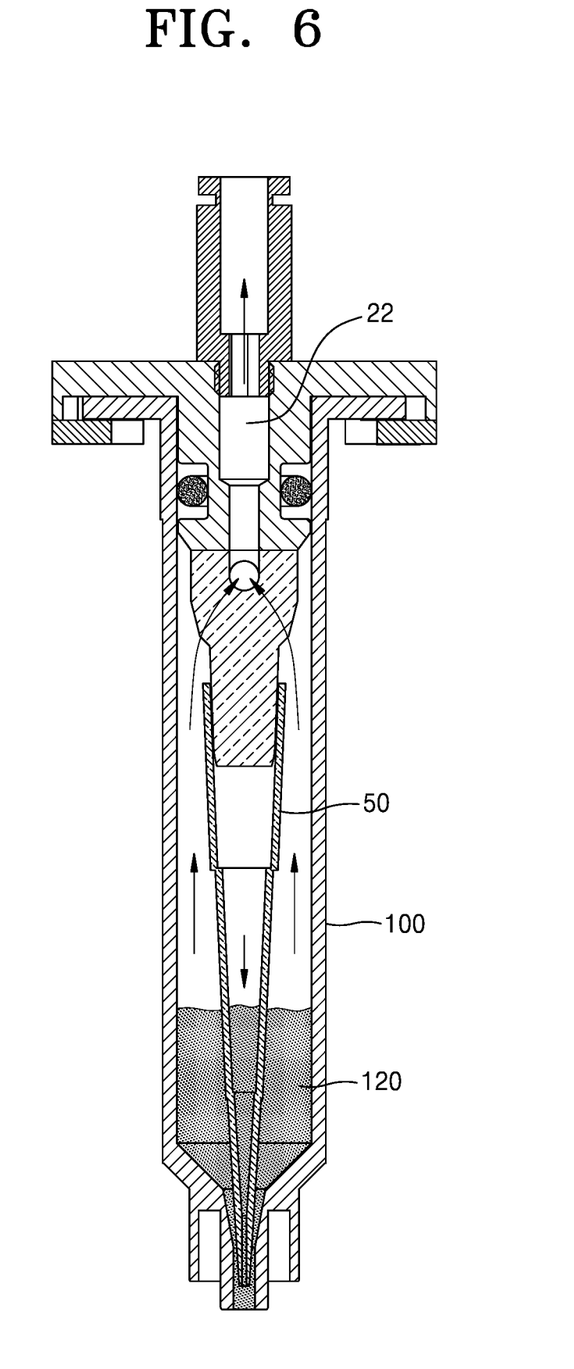
FIG. 6 is a diagram corresponding to FIG. 3 and is a cross-sectional view showing a level of a biomaterial in a state in which a pneumatic pressure supplied to a vent reaches a minimum pressure.
Figure 7:
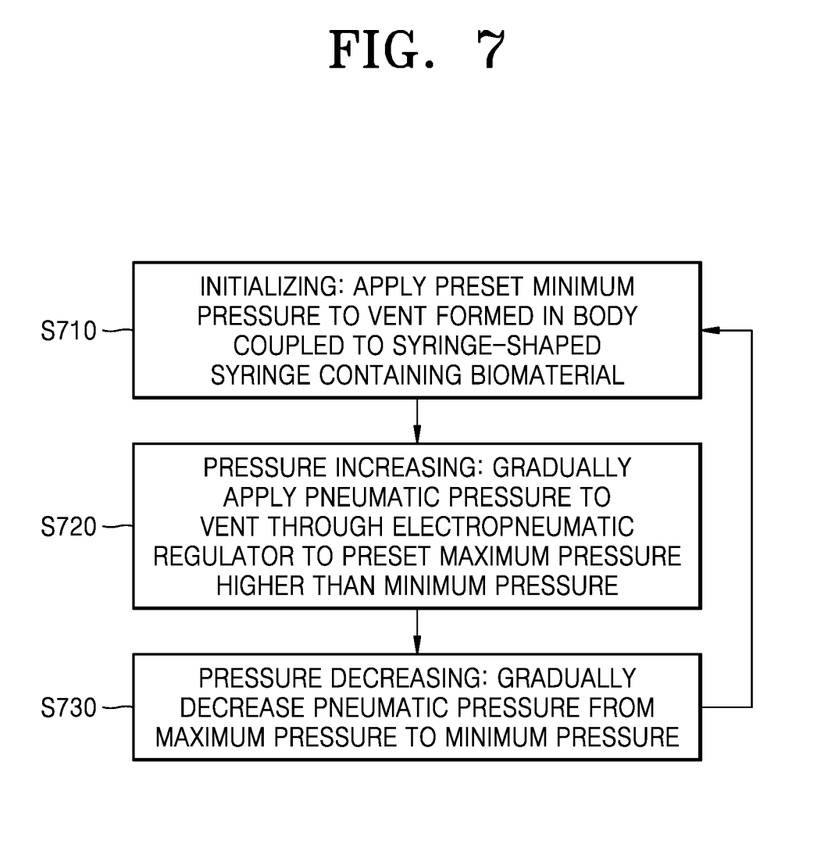
FIG. 7 is a flowchart of a method of maintaining a cell suspension of a biomaterial for a bio 3D printer according to at least one embodiment of the present invention.

FIG. 5 is a diagram corresponding to FIG. 3 and is a cross-sectional view showing a level of a biomaterial in a state in which a pneumatic pressure supplied to a vent reaches a maximum pressure. FIG. 6 is a diagram corresponding to FIG. 3 and is a cross-sectional view showing a level of a biomaterial in a state in which a pneumatic pressure supplied to a vent reaches a minimum pressure. FIG. 7 is a flowchart of a method of maintaining a cell suspension of a biomaterial for a bio 3D printer according to at least one embodiment of the present invention. Arrows shown in FIGS. 5 and 7 schematically show directions in which the pneumatic pressure is applied to the biomaterial.

When a nozzle is closed, the biomaterial 120 accommodated in the syringe 100 generally maintains a cell suspension state for about 3 to 5 minutes. When this time elapses, cell components sink or aggregate into a lower portion of a culture solution, and the cell suspension state is not maintained.

In this case, the electropneumatic regulator 300 periodically changes a pneumatic pressure between preset minimum pressure and maximum pressure so that the cell suspension state is continuously maintained, and supplies the pneumatic pressure to the vent 22. When the nozzle is closed, the biomaterial 120 is not discharged through a lower outlet of the syringe 100.

The apparatus and method for maintaining the cell suspension of the biomaterial for the bio 3D printer according to the present invention sequentially repeats an initializing step (step S710), a pressure increasing step (step S720), and a pressure decreasing step (step S730).

In the initializing step (step S710), the preset minimum pressure is applied to the vent 22 formed in the body 20 coupled to an inlet of the syringe-shaped syringe 100 containing the biomaterial 120. It is preferable to set the minimum pressure to a pressure equal to or higher than, for example, an atmospheric pressure. When the minimum pressure is lower than the atmospheric pressure, there is a possibility that the biomaterial 120 accommodated in the syringe 100 flows back into the vent 22.

The pressure increasing step (step S720) is performed after the initializing step (step S710). In the pressure increasing step (step S720), the pneumatic pressure is gradually applied to the vent 22 through the electropneumatic regulator 300 to the preset maximum pressure higher than the minimum pressure. For example, the maximum pressure may be set to a pressure of 7.5 psi higher than the atmospheric pressure. While the pressure increasing step (step S720) proceeds, the pneumatic pressure supplied to the vent 22 presses a surface of the biomaterial 120 accommodated in the syringe 100 through the air discharge port 32.

Since the biomaterial 120 is an incompressible fluid, the pressure formed by the air discharged from the electropneumatic regulator 300 to the air discharge port 32 through the vent 22 acts equally on the surface of the biomaterial 120 according to Pascal's principle. Accordingly, a part of the biomaterial 120 is pushed into the pipette 50 by the applied pneumatic pressure. Thus, the level of the biomaterial 120 accommodated between an inner wall of the syringe 100 and an outer wall of the pipette 50 decreases, and the level of the biomaterial 120 inside the pipette 50 increases. The level of the biomaterial 120 inside the pipette 50 increases until the pressure inside the syringe 100 and the pressure inside the pipette 50 are balanced.

The pressure decreasing step (step S730) is performed after the pressure increasing step (step S720). In the pressure decreasing step (step S730), the pneumatic pressure gradually decreases from the maximum pressure to the minimum pressure. In this process, the pneumatic pressure supplied from the electropneumatic regulator 300 to the vent 22 is gradually changed from the maximum pressure to the minimum pressure. For example, the minimum pressure may be set to near the atmospheric pressure.

During the pressure decreasing step (step S730), the pneumatic pressure supplied to the vent 22 is gradually lowered. Accordingly, air inside the syringe 100 flows toward the electropneumatic regulator 300 through the air discharge port 32. Thus, the pneumatic pressure that presses the surface of the biomaterial 120 accommodated in the syringe 100 is lowered. Since the biomaterial 120 is an incompressible fluid, the pressure acts equally on the surface of the biomaterial 120 according to the Pascal's principle.

Accordingly, a part of the biomaterial 120 is pushed to the outside of the pipette 50 by the reduced pneumatic pressure. Accordingly, the level of the biomaterial 120 accommodated between the inner wall of the syringe 100 and the outer wall of the pipette 50 increases, and the level of the biomaterial 120 inside the pipette 50 decreases. The level of the biomaterial 120 inside the pipette 50 is lowered until the pressure inside the syringe 100 and the pressure inside the pipette 50 are balanced.

This process is repeated sequentially. As a result, a phenomenon in which the biomaterial 120 is pushed into the pipette 50 and then discharged again repeatedly proceeds. One period including the initializing step (step S710), the pressure increasing step (step S720), and the pressure decreasing step (step S730) may be set to, for example, a few seconds. The period may be set to an arbitrary value according to settings of a user. For example, one period may be set to 2 seconds.

As a result, the biomaterial 120 accommodated in the syringe 100 produces the same effect as the continuous stirring, thereby providing the effect of continuously maintaining a cell suspension state.

As described above, the apparatus and method for maintaining the cell suspension of a biomaterial for a bio 3D printer according to the present invention provides the effect of maintaining a suspension state continuously without agglomeration of the biological material by sequentially increasing and decreasing the pneumatic pressure between a preset minimum pressure from the outside and a preset maximum pressure greater than the minimum pressure through a vent formed in the body coupled to a syringe containing the biomaterial and then repeatedly pushing or discharging the biological material into or from a pipette by the change in the pneumatic pressure applied to the biological material contained in the syringe by the changed in the pneumatic pressure inside the syringe.

As described above, the at least one embodiment of the present invention may provide a cell suspension maintenance method capable of periodically pipetting a biomaterial adhered to a syringe so that the biomaterial contained in the syringe may continuously maintain a suspension state.

The at least one embodiment of the present invention may also provide a cell suspension maintenance apparatus capable of periodically pipetting a biomaterial adhered to a syringe so that the biomaterial contained in the syringe may continuously maintain a suspension state.

The at least one embodiment of the present invention may also provide a cell suspension maintenance system capable of periodically pipetting a biomaterial adhered to a syringe so that the biomaterial contained in the syringe may continuously maintain a suspension state.

The at least one embodiment of the present invention may also provide a bio 3D printer having a cell suspension maintenance function capable of periodically pipetting a biomaterial adhered to a syringe so that the biomaterial contained in the syringe may continuously maintain a suspension state.

While preferred embodiments have been described with reference to the figures, it will be understood by those of ordinary skill in the art that various changes in form and details may be made therein without departing from the spirit and scope as defined by the following claims.

EXPLANATION OF REFERENCE NUMERALS DESIGNATING THE MAJOR ELEMENTS OF THE DRAWINGS

10: apparatus for maintaining a cell suspension of a biomaterial for a bio 3D printer
20: body
22: vent
24: sealing ring coupling groove
25: sealing ring
28: one-touch hose coupling member
30: pipette fixture
32: discharge port
40: syringe fixing arm
42: support arm
44: arm cover
50: pipette
100: syringe
110: upper flange
120: biomaterial
200: hose
300: electropneumatic regulator
400: air dryer
500: air compressor
S710: initializing step
S720: pressure increasing step
S730: pressure decreasing step

The invention claimed is:
1. A suspension maintenance apparatus comprising:
a body detachably coupled to a syringe;
a vent formed inside the body in a longitudinal direction of the syringe;
a pipette fixture extending downward from the body and the pipette fixture having a tapered shape whose outer diameter decreases downwardly;

an air discharge port formed inside the pipette fixture, connected to the vent, and communicated into the syringe, wherein the air discharge port extends in a direction perpendicular to the longitudinal direction of the syringe, and is configured to eject air discharged through the air discharge port toward an inner wall of the syringe;

a syringe fixing arm protruding from the body in a direction perpendicular to the longitudinal direction of the syringe to surround an upper flange of the syringe and fixed to the syringe; and a pipette coupled to the pipette fixture and the pipette having a hollow tapered shape, wherein an inner diameter of the pipette decreases downwardly and having a lower end positioned in an outlet of the syringe, and wherein the pipette has an upper portion coupled to the pipette fixture and completely sealed by the pipette fixture so that air is not injected into the pipette through the upper portion of the pipette.

2. The suspension maintenance apparatus of claim 1, further comprising:

a sealing ring coupling groove formed concavely in a side surface of the body and extending in a circumferential direction of the syringe; and an annular sealing ring coupled to the sealing ring coupling groove extended in the circumferential direction of the syringe, wherein an outer circumferential surface of the sealing ring is coupled to an inner circumferential surface of the syringe in a state of elastic pressurization.

3. The suspension maintenance apparatus of claim 1, wherein the syringe fixing arm comprises a support arm protruding symmetrically around the body in a direction perpendicular to the longitudinal direction of the syringe and the support arm contacting an upper surface of the upper flange of the syringe, and an arm cover contacting a lower surface of the upper flange of the syringe and detachably coupled to the support arm.

4. The suspension maintenance apparatus of claim 1, further comprising an arm cover, wherein the arm cover comprises a separation prevention stopper comprising a protruding member protruding from the arm cover that prevents the syringe fixing arm from being separated from the syringe by connecting the arm cover and a support arm of the syringe fixing arm.

5. The suspension maintenance apparatus of claim 1, further comprising a hose coupling connector configured to couple a hose for supplying a pneumatic pressure to an upper portion of the vent.

6. A syringe comprising a suspension maintenance apparatus, wherein the suspension maintenance apparatus comprises:

a body detachably coupled to the syringe;

a vent formed inside the body in a longitudinal direction of the syringe;

a pipette fixture extending downward from the body and the pipette fixture having a tapered shape whose outer diameter decreases downwardly;

an air discharge port formed inside the pipette fixture, connected to the vent, and communicated into the syringe, wherein the air discharge port extends in a direction perpendicular to the longitudinal direction of the syringe, and is configured to eject air discharged through the air discharge port toward an inner wall of the syringe;

a syringe fixing arm protruding from the body in a direction perpendicular to the longitudinal direction of the syringe to surround an upper flange of the syringe and fixed to the syringe; and a pipette coupled to the pipette fixture and the pipette having a hollow tapered shape, wherein an inner diameter of the pipette decreases downwardly and having a lower end positioned in an outlet of the syringe, and wherein the pipette has an upper portion coupled to the pipette fixture and completely sealed by the pipette fixture so that air is not injected into the pipette through the upper portion of the pipette.

7. A bio 3D printer comprising a syringe comprising a suspension maintenance apparatus and the syringe having an outlet connected to a nozzle injecting a biomaterial; and a pneumatic pressure supply apparatus for supplying a preset pneumatic pressure to the suspension maintenance apparatus, wherein the suspension maintenance apparatus comprises:

a body detachably coupled to the syringe;

a vent formed inside the body in a longitudinal direction of the syringe;

a pipette fixture extending downward from the body and the pipette fixture having a tapered shape whose outer diameter decreases downwardly;

an air discharge port formed inside the pipette fixture, connected to the vent, and communicated into the syringe, wherein the air discharge port extends in a direction perpendicular to the longitudinal direction of the syringe, and is configured to eject air discharged through the air discharge port toward an inner wall of the syringe;

a syringe fixing arm protruding from the body in a direction perpendicular to the longitudinal direction of the syringe to surround an upper flange of the syringe and fixed to the syringe; and a pipette coupled to the pipette fixture and the pipette having a hollow tapered shape, wherein an inner diameter of the pipette decreases downwardly and having a lower end positioned in the outlet of the syringe, and wherein the pipette has an upper portion coupled to the pipette fixture and completely sealed by the pipette fixture so that air is not injected into the pipette through the upper portion of the pipette.

8. The bio 3D printer of claim 7, wherein the pneumatic pressure supply apparatus comprises an air compressor for supplying air at a pressure, wherein the pressure is higher than a predetermined threshold, and an electropneumatic regulator having one side connected to the suspension maintenance apparatus and an other side connected to the air compressor to convert the air supplied at the pressure from the air compressor to a preset pneumatic pressure and supplying the pneumatic pressure to the suspension maintenance apparatus.

9. The bio 3D printer of claim 7, wherein the pneumatic pressure supply apparatus comprises a pump.

10. The bio 3D printer of claim 8, further comprising an air dryer installed between the electropneumatic regulator and the air compressor to remove water vapor contained in the air supplied at the pressure from the air compressor.

11. The bio 3D printer of claim 8, further comprising a controller controlling the electropneumatic regulator to periodically apply pneumatic pressure to the suspension maintenance apparatus at a preset minimum pressure and a preset maximum pressure during a time when the biomaterial accommodated in the syringe is not discharged downward from the syringe.

12. The bio 3D printer of claim 9, further comprising a controller controlling the precision pump to periodically apply pneumatic pressure to the suspension maintenance apparatus at a preset minimum pressure and a preset maximum pressure during a time when the biomaterial accommodated in the syringe is not discharged downward from the syringe.

13. The bio 3D printer of claim 11, wherein the minimum pressure is equal to or higher than an atmospheric pressure, and the maximum pressure is a pressure higher than the atmospheric pressure by a predetermined pressure and higher than the minimum pressure.

14. A method of maintaining a suspension state of a biomaterial for a bio 3D printer accommodated in a syringe by controlling an electropneumatic regulator in a suspension maintenance apparatus, wherein the bio 3D printer includes the syringe including the suspension maintenance apparatus:

the suspension state maintenance method comprising:
applying a predetermined minimum pressure to the suspension maintenance apparatus coupled to the syringe containing the biomaterial, wherein the suspension maintenance apparatus comprises:
a body detachably coupled to the syringe,
a vent formed inside the body in a longitudinal direction of the syringe,
a pipette coupled to a pipette fixture and the pipette fixture extending downward from the body and the pipette fixture having a tapered shape and an outer diameter of the pipette decreases downwardly,
an air discharge port formed inside the pipette fixture, connected to the vent, and communicated into the syringe, wherein the air discharge port extends in a direction perpendicular to the longitudinal direction of the syringe, and is configured to eject air discharged through the air discharge port toward an inner wall of the syringe,
a syringe fixing arm protruding from the body in a direction perpendicular to the longitudinal direction of the syringe to surround an upper flange of the syringe and fixed to the syringe, and
the pipette having a hollow tapered shape and an inner diameter of the pipette decreases downwardly and having a lower end positioned in an outlet of the syringe, wherein the pipette has an upper portion coupled to the pipette fixture and completely sealed by the pipette fixture so that air is not injected into the pipette through the upper portion of the pipette;
gradually increasing the pneumatic pressure in the suspension maintenance apparatus to a maximum pressure greater than the minimum pressure;
gradually reducing the pneumatic pressure from the maximum pressure to the minimum pressure, wherein the pneumatic pressure is supplied from the electropneumatic regulator of the bio 3D printer and the bio 3D printer comprises:

the syringe having the outlet connected to a nozzle injecting the biomaterial,
an air compressor for supplying air at a pressure, wherein the pressure is higher than a predetermined threshold, and
the electropneumatic regulator having one side connected to the suspension maintenance apparatus and an other side connected to the air compressor to convert the air supplied at a high pressure from the air compressor to a preset pneumatic pressure and supplying the pneumatic pressure to the suspension maintenance apparatus; and
repeating increasing the pneumatic pressure and reducing the pneumatic pressure for a predetermined period.

15. The method of claim 14, wherein the minimum pressure is equal to or higher than an atmospheric pressure, and the maximum pressure is a pressure higher than the atmospheric pressure by a predetermined pressure and higher than the minimum pressure.

16. A suspension maintenance apparatus comprising:
a body detachably coupled to a syringe;
a vent formed inside the body in a longitudinal direction of the syringe;
a pipette fixture extending downward from the body and the pipette fixture having a tapered shape whose outer diameter decreases downwardly;
an air discharge port formed inside the pipette fixture, connected to the vent, and communicated into the syringe, wherein the air discharge port extends in a direction perpendicular to the longitudinal direction of the syringe, and is configured to eject air discharged through the air discharge port toward an inner wall of the syringe;
a syringe fixing arm protruding from the body in a direction perpendicular to the longitudinal direction of the syringe to surround an upper flange of the syringe and fixed to the syringe;
a pipette coupled to the pipette fixture and the pipette having a hollow tapered shape whose inner diameter decreases downwardly and having a lower end positioned in an outlet of the syringe, wherein the pipette has an upper portion coupled to the pipette fixture and completely sealed by the pipette fixture so that air is not injected into the pipette through the upper portion of the pipette;
a sealing ring coupling groove formed concavely in a side surface of the body and extending in a circumferential direction of the syringe; and
an annular sealing ring coupled to the sealing ring coupling groove extended in the circumferential direction of the syringe, wherein an outer circumferential surface of the sealing ring is coupled to an inner circumferential surface of the syringe in a state of elastic pressurization.

* * * * *